United States Patent
McIntosh et al.

(10) Patent No.: US 6,685,936 B2
(45) Date of Patent: Feb. 3, 2004

(54) SUPPRESSOR CELLS INDUCED BY CULTURE WITH MESENCHYMAL STEM CELLS FOR TREATMENT OF IMMUNE RESPONSES IN TRANSPLANTATION

(75) Inventors: Kevin McIntosh, Ellicott City, MD (US); Elena Klyushnenkova, Baltimore, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/415,627

(22) Filed: Oct. 12, 1999

(65) Prior Publication Data

US 2002/0034504 A1 Mar. 21, 2002

(51) Int. Cl.[7] ................................................ A01N 63/00
(52) U.S. Cl. .............................. 424/93.71; 424/278.1; 424/154.1; 435/373
(58) Field of Search ........................ 424/154.1, 93.71, 424/278.1; 435/373

(56) References Cited

U.S. PATENT DOCUMENTS 5,788,968 A * 8/1998 Weiner et al.

OTHER PUBLICATIONS

Immunobiology, Janeway et al. p. 11:35, 1994.*
Gasset et al. Transplantation 54:1048–1053, 1992.*
Pritchard et al. J. Immunol. 149:45–52, 1992.*

* cited by examiner

*Primary Examiner*—G. R. Ewoldt
(74) *Attorney, Agent, or Firm*—Elliot M. Olstein; Raymond J. Lillie (57) ABSTRACT

A method of reducing an immune response to a transplant in a recipient by treating said recipient with an amount of suppressor T cells effective to reduce or inhibit host rejection of the transplant. The suppressor T cells can be administered before, at the same time as, or after the transplant. Also disclosed is a method of inducing a reduced immune response against a host by foreign tissue, i.e., graft versus host disease, by treatment with suppressor T cells.

14 Claims, 10 Drawing Sheets

FIG. 1

T1 - cultured alone
T2 - cultured with MSC, non-fractioned
T3 - cultured with MSC, CD8-depleted

SUPPRESSOR CELLS INDUCED BY CULTURE WITH MESENCHYMAL STEM CELLS FOR TREATMENT OF IMMUNE RESPONSES IN TRANSPLANTATION

The present invention relates to inhibiting an immune response to an alloantigen and further relates to inhibiting and/or preventing reactivation of previously activated T cells. More particularly, the present invention relates to the field of preventing, reducing or treating an immune response caused by immune effector cells to foreign tissue and/or cells and/or organs. The invention further relates to preventing, reducing or treating transplant rejection and/or graft versus host reaction.

BACKGROUND OF THE INVENTION

Tolerance is the acquired lack of specific responsiveness to an antigen to which an immune response would normally occur. Typically, to induce tolerance, there must be an exposure to a tolerizing antigen, which results in the death or functional inactivation of certain lymphocytes. Complete tolerance is characterized by the lack of a detectable immune response to the second antigenic challenge. Partial tolerance is typified by the quantitative reduction of an immune response.

Unfortunately, the immune system does not distinguish beneficial intruders, such as transplanted tissue, from those that are harmful, and thus the immune system rejects transplanted tissue or organs. Rejection of transplanted organs is significantly mediated by alloreactive T cells present in the host which recognize donor alloantigens or xenoantigens.

At present, in order to prevent or reduce an immune response against a transplant, patients are treated with powerful immunosuppressive drugs. The infusion of individuals with drugs that prevent or suppress a T-cell immune response does inhibit transplant rejection, but can also result in general immune suppression, toxicity and even death due to opportunistic infections. Because of the toxicity and incomplete response rate to conventional treatment of donor tissue rejection, alternative approaches are needed to treat patients who cannot withstand or do not respond to current modes of drug therapy.

Accordingly, there is a need for the prevention and/or reduction of an unwanted immune response by a host to a transplant by immune effector cells as a method to avert host rejection of donor tissue. Also advantageous would be a method to eliminate or reduce an unwanted immune response by a donor tissue against a recipient tissue, known as graft-versus-host disease.

SUMMARY OF THE INVENTION

It has been discovered that mesenchymal stem cells (MSCs) can induce allo-activated T-cells to become suppressive for allogeneic responses, and that human suppressor cells can be used in transplantation to ameliorate a response by the immune system such that an immune response to an antigen(s) will be reduced or eliminated.

In accordance with one aspect of the invention, there is provided a method for reducing or suppressing an immune response caused by T cells responding to an alloantigen, in particular allogeneic tissue, organ or cells, wherein the immune response is reduced or suppressed by the use of suppressor T cells. The suppressor T cells may be autologous to the T cells (obtained from the same host), or may be allogeneic to the T-cells.

In accordance with another aspect of the present invention there is provided a process for preventing restimulation of activated T cells (activated against an alloantigen, in particular an allogeneic organ, tissue or cells) by contacting activated T cells with suppressor T cells in an amount effective to prevent and/or reduce a subsequent T cell response to a foreign antigen. The mesenchymal stem cells that are used may be autologous to the T cells, or may be allogeneic to the T-cells. Preferably, the mesenchymal stem cells are autologous to the T-cells.

In accordance with another aspect of the present invention, suppressor T cells are used to suppress or ameliorate an immune response to a transplant (tissue, organ, cells, etc.) by administering to the transplant recipient suppressor T cells in an amount effective to suppress or ameliorate an immune response against the transplant. The suppressor T cells may be autologous to the transplant recipient, or the suppressor T-cells may be allogeneic to the transplant recipient. Preferably, the suppressor T-cells are autologous to the transplant recipient.

Accordingly, one method of the present invention provides contacting the recipient of donor tissue with autologous suppressor T cells. In one embodiment of this aspect, the method involves administering suppressor T cells to the recipient of donor tissue. The suppressor T cells can be administered to the recipient before or at the same time as the transplant or subsequent to the transplant.

The suppressor T cells can also be administered to the recipient as part of the transplant. To this objective, the present invention provides a method for reducing or ameliorating an immune response by providing to the recipient donor tissue or organ that is perfused with or includes suppressor T cells autologous to the T cells. The suppressor T cells ameliorate an immune response by the recipient's T cells against the foreign tissue when it is transplanted into the recipient.

In another embodiment, the method of the present invention provides treating a patient who has received a transplant, in order to reduce the severity of or eliminate a rejection episode against the transplant, by administering to the recipient of donor tissue suppressor T cells after the donor tissue has been transplanted into the recipient. The suppressor T cells preferably are autologous to the recipient. The presentation of suppressor T cells to a recipient undergoing an adverse immune response to a transplant induces nonresponsiveness of T cells to further antigenic stimulation thereby reducing or eliminating an adverse response by activated T cells to donor tissue or organ.

In a further aspect of the present invention, there is provided a method of reducing an immune response by donor tissue, organ or cells against a recipient, i.e. graft versus host response, comprising treating the donor tissue, organ or cells with suppressor T cells ex vivo prior to transplantation of the tissue, organ or cells into the recipient. The suppressor T cells reduce the responsiveness of T cells in the transplant that may be subsequently activated against recipient antigen presenting cells such that the transplant may be introduced into the recipient's (host's) body without the occurrence of, or with a reduction in, an adverse response of the transplant to the host. Thus, what is known as "graft versus host" disease may be averted.

In a preferred embodiment, the donor transplant may be first exposed to recipient or third party tissue or cells ex vivo, to activate the T cells in the donor transplant. The donor transplant is then contacted with suppressor T cells. The suppressor T cells will reduce or inhibit an adverse secondary immune response by T cells in the donor transplant against antigenic stimulation by the recipient when the donor transplant is subsequently placed into the recipient.

The suppressor T cells can be obtained from the recipient prior to the transplant. The suppressor T cells can be isolated and stored frozen until needed. The suppressor T cells may also be culture-expanded to desired amounts and stored until needed. The suppressor T cells are administered to the recipient in an amount effective to reduce or eliminate an ongoing adverse immune response caused by the donor transplant against the recipient (host). The presentation of the suppressor T cells to the recipient undergoing an adverse immune response caused by a transplant inhibits the ongoing response and prevents restimulation of the T cells thereby reducing or eliminating an adverse response by activated T cells to recipient tissue.

Thus, in accordance with preferred embodiments of the present invention, human suppressor T cells are employed to treat transplant rejection and or graft versus host disease as a result of a transplant and or to prevent or reduce transplant rejection and or graft versus host disease. Human suppressor T cells may also be employed to facilitate the use of xenogeneic grafts or transplants.

BRIEF DESCRIPTION OF THE DRAWINGS

FIG. 2 shows the level of suppression of an ongoing mixed lymphocyte reaction by suppressor T cells at day 0 (FIG. 2A), day 1 (FIG. 2B) and day 2 (FIG. 2C) after addition of the suppressor T cells to the reaction cultures. The stimulator cells in the mixed lymphocyte reaction are from the same donor as the stimulator cells used to generate the suppressor T cells. Suppressor T cells (T2) suppressed an on-going mixed lymphocyte reaction early and at very low cell number per well. CD8 cell depleted cell population (T3) resulted in delayed and only partial suppression. T cells cultured without MSCs (T1) did not suppress, and even enhanced the mixed lymphocyte reaction.

FIG. 3 shows the level of suppression of an ongoing mixed lymphocyte reaction by suppressor T cells at day 0 (FIG. 3A), day 1 (FIG. 3B) and day 2 (FIG. 3C) after addition of the suppressor T cells to the reaction cultures. The stimulator cells in the mixed lymphocyte reaction are from a third party donor (different donor than the original stimulator cell donor and suppressor T cell donor). Suppressor T cells (T2) suppressed an on-going mixed lymphocyte reaction early and at very low cell number per well. CD8 cell depleted cell population (T3) resulted in delayed and only partial suppression. T cells cultured without MSCs (T1) did not suppress, and even enhanced the mixed lymphocyte reaction.

FIG. 4 shows the level of suppression of PHA proliferative response by suppressor T cells at day 1 (FIG. 4A), day 2 (FIG. 4B) and day 3 (FIG. 4C). Suppressor T cells suppressed PHA-induced proliferation of autologous PBMCs whereas T cells cultured alone accelerated the PHA response. Depletion of CD8 cells resulted in delayed and only partial suppression.

DETAILED DESCRIPTION OF THE INVENTION

As defined herein suppressor T cells are T cells which have been primed, for example, in a mixed lymphocyte reaction by exposure to an alloantigen, and subsequently cultured with mesenchymal stem cells (autologous or allogeneic to the T cells—same as stimulator or third party). These suppressor T cells are not restimulated when placed again in a mixed lymphocyte reaction and exposed to an alloantigen either the same or third party alloantigen as the original stimulator cells.

Donor antigen refers to antigens expressed by the donor tissue to be transplanted into the recipient. Alloantigens are antigens which differ from antigens expressed by the recipient. Donor tissue, organs or cells to be transplanted is the transplant. Examples of transplants include, but are not limited to, skin, bone marrow, and solid organs such as heart, pancreas, kidney, lung and liver. The pancreas and liver may be reduced to single cell suspensions for transplant.

The inventors have discovered that suppressor T cells can suppress an MLR between allogeneic cells. Suppressor T cells actively reduced the allogeneic T cell response in mixed lymphocyte reactions in a dose dependent manner.

Accordingly, the present invention provides a method of reducing, inhibiting or eliminating an immune response by administering suppressor T cells to a recipient of a donor tissue, organ or cells. In one embodiment, the suppressor T cells are administered to the recipient contemporaneously with the transplant. Alternatively, the suppressor T cells can be administered prior to the administration of the transplant. For example, the suppressor T cells can be administered to the recipient about 3 to 7 days before transplantation of the donor tissue.

Thus, suppressor T cells can be used to condition a recipient's immune system to donor or foreign tissue by administering to the recipient, prior to, or at the same time as transplantation of the donor tissue, suppressor T cells in an amount effective to reduce or eliminate an immune response against the transplant by the recipient's T cells. The suppressor T cells affect the T cells of the recipient such that the T cell response is reduced or eliminated when presented with donor or foreign tissue. Thus, host rejection of the transplant may be avoided or the severity thereof reduced.

Accordingly, the present invention provides a method for treating a patient who is undergoing an adverse immune response to a transplant by administering suppressor T cells to such patient in an amount effective to reduce or suppress the immune response. The suppressor T cells may be obtained from the transplant recipient, from the transplant donor, or from a third party.

In another aspect, the present invention provides a method to reduce or inhibit or eliminate an immune response by a donor transplant against a recipient thereof (graft versus host). Accordingly, the invention provides contacting a donor organ or tissue with suppressor T cells prior to transplant. The suppressor T cells ameliorate, inhibit or reduce an adverse response by the donor transplant against the recipient.

In a preferred embodiment, prior to transplant the donor transplant is treated with allogeneic (recipient) tissue or cells which activate the T cells in the donor transplant. The donor transplant is then treated with autologous suppressor T cells prior to transplant. The suppressor T cells prevent restimulation, or induce hyporesponsiveness, of the T cells to subsequent antigenic stimulation.

Thus, in the context of bone marrow (hematopoietic stem cell) transplantation, attack of the host by the graft can be reduced or eliminated. Donor marrow can be pretreated with donor suppressor T cells prior to implant of the bone marrow or peripheral blood stem cells into the recipient. In a preferred embodiment, the donor marrow is first exposed to recipient tissue/cells and then treated with suppressor T cells. Although not being limited thereto, it is believed that the initial contact with recipient tissue or cells functions to activate the T cells in the marrow. Subsequent treatment with the suppressor T cells inhibits or eliminates further activation of the T cells in the marrow, thereby reducing or eliminating an adverse affect by the donor tissue, i.e. the therapy reduces or eliminates graft versus host response.

In a further embodiment, a transplant recipient suffering from graft versus host disease may be treated to reduce or eliminate the severity thereof by administering to such recipient suppressor T cells in an amount effective to reduce or eliminate a graft rejection of the host. The suppressor T cells inhibit or suppress the activated T cells in the donor tissue from mounting an immune response against the recipient, thereby reducing or eliminating a graft versus host response.

The recipient's suppressor T cells may be obtained from the transplant donor or the recipient or a third party prior to the transplantation and may be stored and/or culture-expanded to provide a reserve of suppressor T cells in sufficient amounts for treating an ongoing graft attack against host.

In yet another method of the present invention, the donor tissue is exposed to suppressor T cells such that the suppressor T cells integrate into the organ graft itself prior to transplantation. In this situation, an immune response against the graft caused by any alloreactive recipient cells that escaped standard treatment to prevent transplant rejection, e.g., drug-mediated immunosuppression, would be suppressed by the suppressor T cells present in the graft. The suppressor T cells are preferably autologous to the recipient.

In accordance with the methods of the present invention described herein, it is contemplated that the suppressor T cells of the present invention can be used in conjunction with current modes of treating donor tissue rejection or graft versus host disease. An advantage of such use is that by ameliorating the severity of the immune response in a transplant recipient, the amount of drug used in treatment and/or the frequency of administration of drug therapy can be reduced, resulting in alleviation of general immune suppression and unwanted side effects.

It is further contemplated that only a single treatment with the suppressor T cells of the present invention may be required, eliminating the need for chronic immunosuppressive drug therapy. Alternatively, multiple administrations of suppressor T cells may be employed.

Accordingly, the invention described herein provides for preventing or treating transplant rejection by administering the suppressor T cells in a prophylactic or therapeutically effective amount for the prevention or treatment or amelioration of transplant rejection of an organ, tissue or cells from the same species, or a xenograft organ or tissue transplant and or graft versus host disease.

Administration of a single dose of suppressor T cells may be effective to reduce or eliminate the T cell response to tissue allogeneic to the T cells or to "non-self" tissue, particularly in the case where the T lymphocytes retain their nonresponsive character (i.e., tolerance or anergy) to allogeneic cells after being separated from the suppressor T cells.

The dosage of the suppressor T cells varies within wide limits and will, of course be fitted to the individual requirements in each particular case. In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art. The suppressor T cells can be administered by a route which is suitable for the tissue, organ or cells to be transplanted. They can be administered systemically, i.e., parenterally, by intravenous injection or can be targeted to a particular tissue or organ, such as bone marrow. The suppressor T cells can be administered via a subcutaneous implantation of cells or by injection of stem cell into connective tissue, for example muscle.

The cells can be suspended in an appropriate diluent, at a concentration of from about 0.01 to about $5\times10^6$ cells/ml. Suitable excipients for injection solutions are those that are biologically and physiologically compatible with the cells and with the recipient, such as buffered saline solution or other suitable excipients. The composition for administration must be formulated, produced and stored according to standard methods complying with proper sterility and stability.

Although the invention is not limited thereof, mesenchymal stem cells can be isolated, preferably from bone marrow, purified, and expanded in culture, i.e. in vitro, to obtain sufficient numbers of cells for use in the methods described herein. Mesenchymal stem cells, the formative pluripotent blast cells found in the bone, are normally present at very low frequencies in bone marrow (1:100,000) and other mesenchymal tissues. See, Caplan and Haynesworth, U.S. Pat. No. 5,486,359. Gene transduction of mesenchymal stem cells is disclosed in Gerson et al U.S. Pat. No. 5,591,625.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

The mixed lymphocyte reaction measures the compatibility of the donor's surface antigens and is an indication of the likelihood of rejection of donor tissue. Cell surface antigens responsible for eliciting transplant rejection are class I and class II MHC antigens. T cells are alloreactive to foreign MHC antigens. Class I and II MHC molecules stimulate the mixed lymphocyte reaction.

EXAMPLES

Peripheral blood mononuclear cells (PBMC) were prepared by density gradient centrifugation on Ficoll-Paque (Pharmacia). Aliquots of cells were frozen in 90% FCS with 10% DMSO and stored in liquid nitrogen. After thawing, the cells were washed twice with MSC medium (DMEM with low glucose and 10% FCS) and re-suspended in assay medium (ISCOVE'S with 25 mM Hepes, 1 mM sodium pyruvate, 100 µM non-essential amino acids, 100 U/ml penicillin, 100 µg/ml streptomycin, 0.25 µg/ml amphotericin B, $5.5\times10^{-5}$M 2-mercaptoethanol (all reagents from GibcoBLR) and 5% human AB serum (Sigma, MLR tested)).

To prepare the T cell-enriched fraction, PBMCs from donor 155 were depleted of monocytes and B cells by immunomagnetic negative selection. PBMCs were incubated with mouse anti-human CD19 and CD14 mAbs (no azide/low endotoxin (NA/LE) format) followed by biotin-conjugated goat anti-mouse IgG (multiple adsorption) Ab (all reagents from Pharmingen) and streptavidin microbeads (Miltenyi Biotec). Cells were then separated using a magnetic cell sorter (MACS, Miltenyi Biotec).

PBMC from donor 413 were X-ray irradiated with 3600 rad (12 min at 70 kV) using Cabinet X ray system (Faxitron X ray, Buffalo Grove, Ill.).

Activation of T cells:

T cells ($15 \times 10^6$/dish) from donor 155 were cultured in 10 cm tissue culture dishes with PBMC ($15 \times 10^6$ cells/dish) from donor 413 for 7 days. The cells were incubated at 37° C. in 5% $CO_2$ atmosphere for 7 days.

Co-culture with MSCs:

Human MSCs were isolated from donor 273 from bone marrow as described in U.S. Pat. No. 5,486,359 and were maintained in culture with MSC medium and were used at passages from 3 to 6. Cells were lifted using 0.05% Trypsin/EDTA solution, washed once with MSC medium. The MSCs (d 273) were plated at $1.0 \times 10^6$ cells/dish in 10 cm tissue culture dishes, cultured for 4 days, and washed 4 times with PBS-D prior to adding activated T cells (d155). T cells (d155) activated in the MLR for 7 days, were collected washed once with MSC medium and re-suspended in assay medium and transferred to the dishes with the pre-plated MSCs ($0.5 \times 10^6$ cells/ml, $1.0 \times 10^7$ cells/dish) for 3 days at 37° C. in 5% $CO_2$ atmosphere. In control cultures activated T cells were cultured without MSCs at the same density (the "T1" population). Cells cultured with MSCs are the "T2" population; the "T3" population was depleted of CD8+ cells as described hereinbelow.

Immunomagnetic Depletion and FACS staining:

at the end of culture with MSCs (10 days after initiation of primary culture), T cells were recovered and washed. These are the "suppressor T cells" ("T2 population"). CD8 cells were depleted by negative immunomagnetic selection with anti-CD8 MicroBeads (Miltenyi Biotec) (CD8 depleted="T3" population). Aliquots of cells collected before and after depletion were stained with anti-CD4-PE and anti-CD8-APC antibodies (Caltag) and analyzed by FACS.

Re-stimulation: T cells activated in MLR for 7 days and cultured without MSCs (T1) for 3 days, or cultured with MSCs (non-fractionated ("T2") or CD8 depleted ("T3")) were recovered and re-stimulated with irradiated PBMCs autologous to original stimulator (donor 413) or autologous to responder (donor 155). Cells were plated at $5 \times 10^4$ cells/well each in 96-well tissue culture plates. Alternatively, $5 \times 10^4$ T cells were stimulated with PHA (5 µg/ml).

Cultures were pulsed with [$H^3$]TdR (Amersham) (5 Ci/mmol, 1 µCi/well) for 18 hours immediately after plating, or incubated for 1, 2, 3 or 4 days and then pulsed with [$H^3$]TdR for an additional 18 hours. Cultures were collected using Harvester 96 (Tomtec), filters were analyzed using Microbeta Trilux liquid scintillation and luminescence counter (E. G. & G Wallac).

Figure 1:
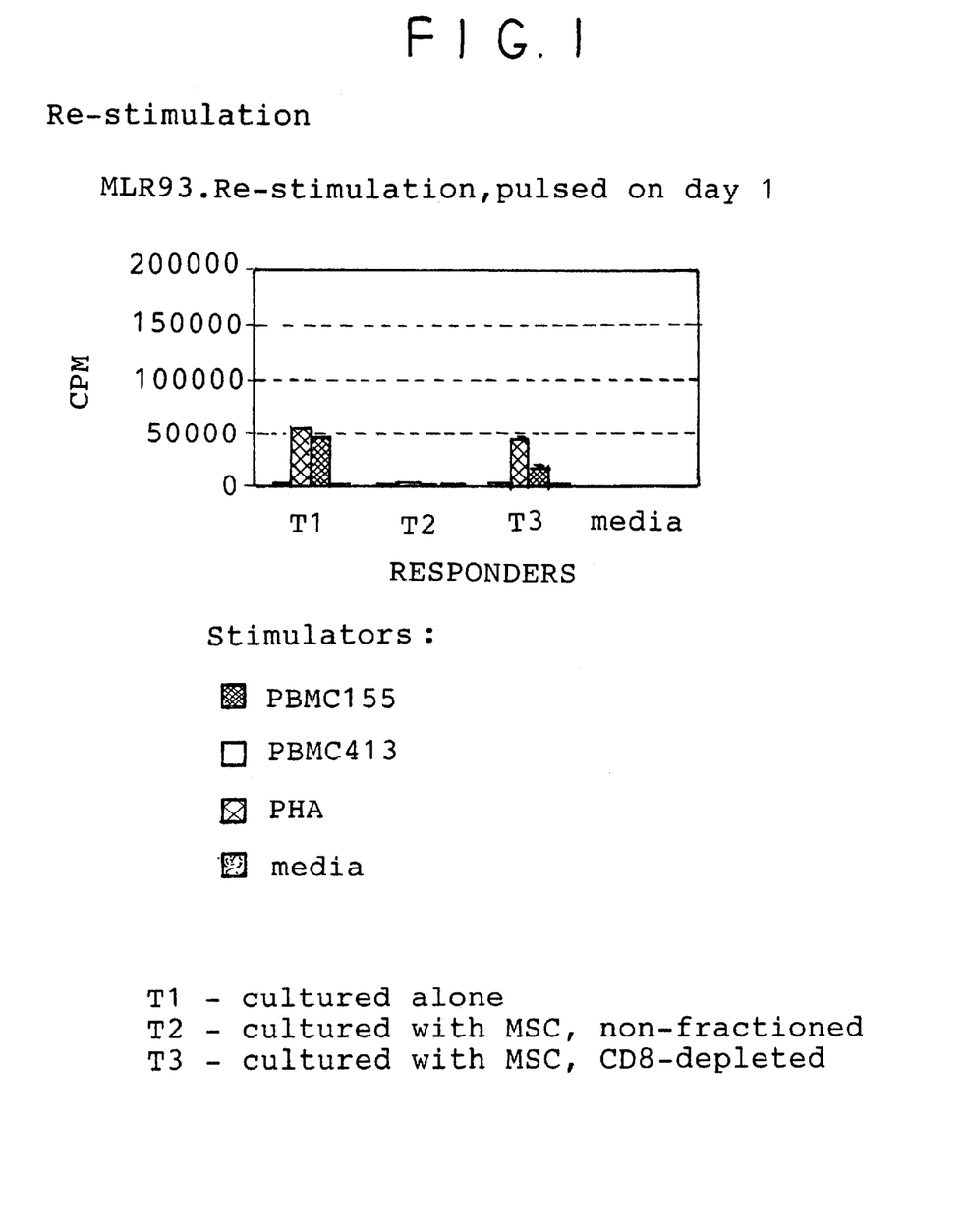
FIG. 1 shows the level of restimulation of suppressor T cells in a mixed lymphocyte reaction using original donor stimulator cells (same donor stimulators used to generate the suppressor T cells) at day 0. Suppressor T cells (T2) did not respond to restimulation with original donor PBMCs or phytohemagglutin (PHA). CD8 cell depleted T cell population (T3) resulted in partial restoration of responsiveness. T cells cultured without MSCs (T1) responded well in the secondary mixed lymphocyte reaction and to PHA.

The results are shown in FIG. 1. Suppressor T cells (T2) did not respond to re-stimulation with original donor PBMCs or PHA. Culture with cells depleted of CD8+ cells from the suppressor T cell population (T3) resulted in partial restoration of responsiveness. T cells cultured without MSCs (T1) responded well in the secondary mixed lymphocyte reaction and to PHA.

Suppression of Ongoing MLR by Suppressor T Cells

An MLR was set up in 96-well tissue culture plates 4 days prior to adding suppressor T cells. In MLR, $1.5 \times 10^5$ responder T cells were mixed with the same number of irradiated stimulator cells. T cells from donor 155 (autologous to suppressor T cells) were prepared from PBMC by negative immunomagnetic selection with anti-CD14 and anti-CD19 MicroBeads. Stimulator PBMCs were from donor 413 (same as the stimulator for suppressor T cell generation) or from donor 273 (third party to supressors). T cells from donor 155 pre-activated by irradiated PBMCs from donor 413 for 7 days, and cultured alone or with MSCs from donor 273 for 3 days (non-fractionated or CD8 depleted) were used as suppressors. After 4 days of culture, suppressor T cells were added at different numbers per well (from $5 \times 10^4$ cells/well to $1.56 \times 10^3$ cells/well). Cultures were pulsed with [$H^3$]TdR (5 Ci/mmol, 1 µCi/well) for 18 hours immediately after plating, or incubated for 1 or 2 days and then pulsed with [$H^3$]TdR for an additional 18 hours.

Figure 2A:
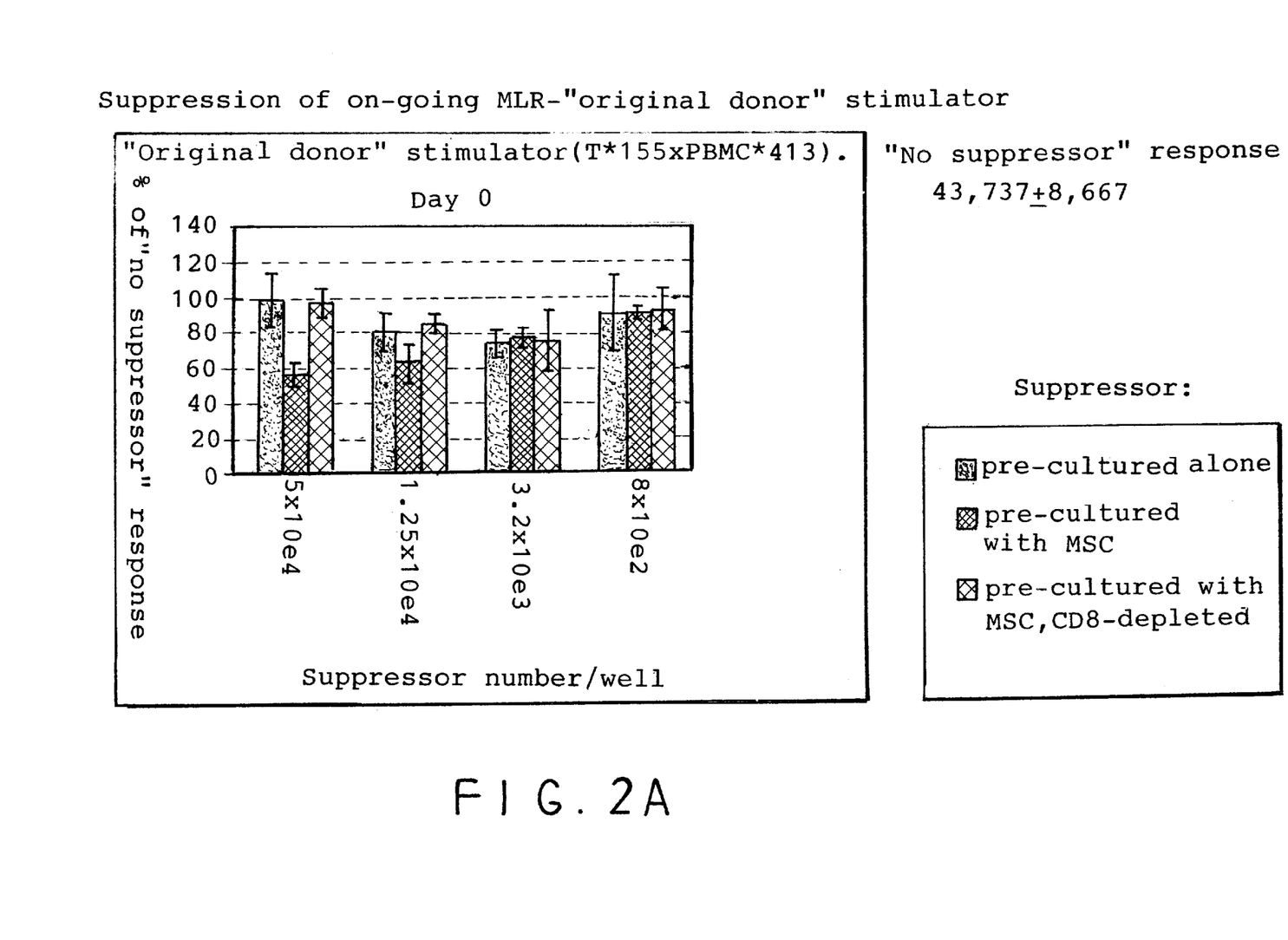
Figure 2B:
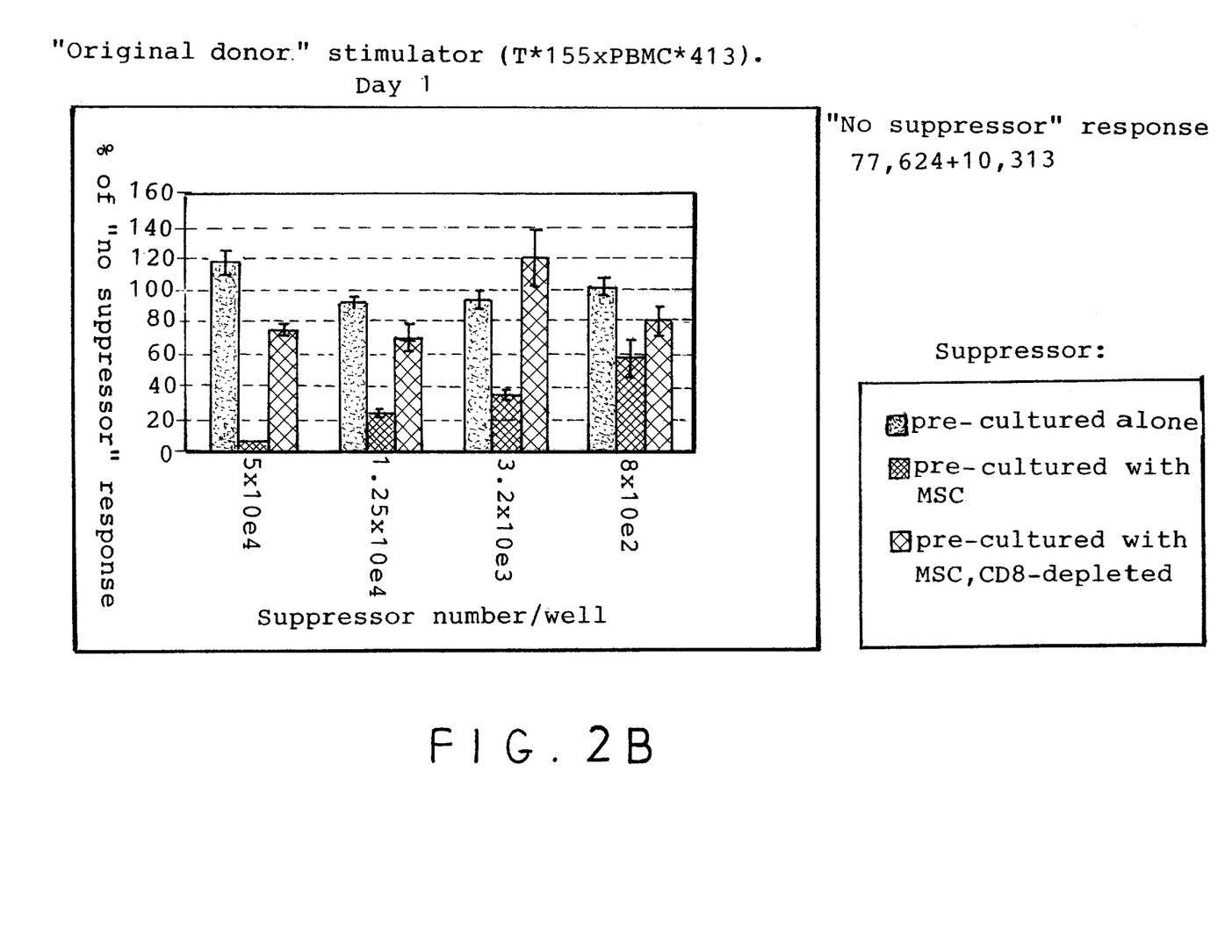
Figure 2C:
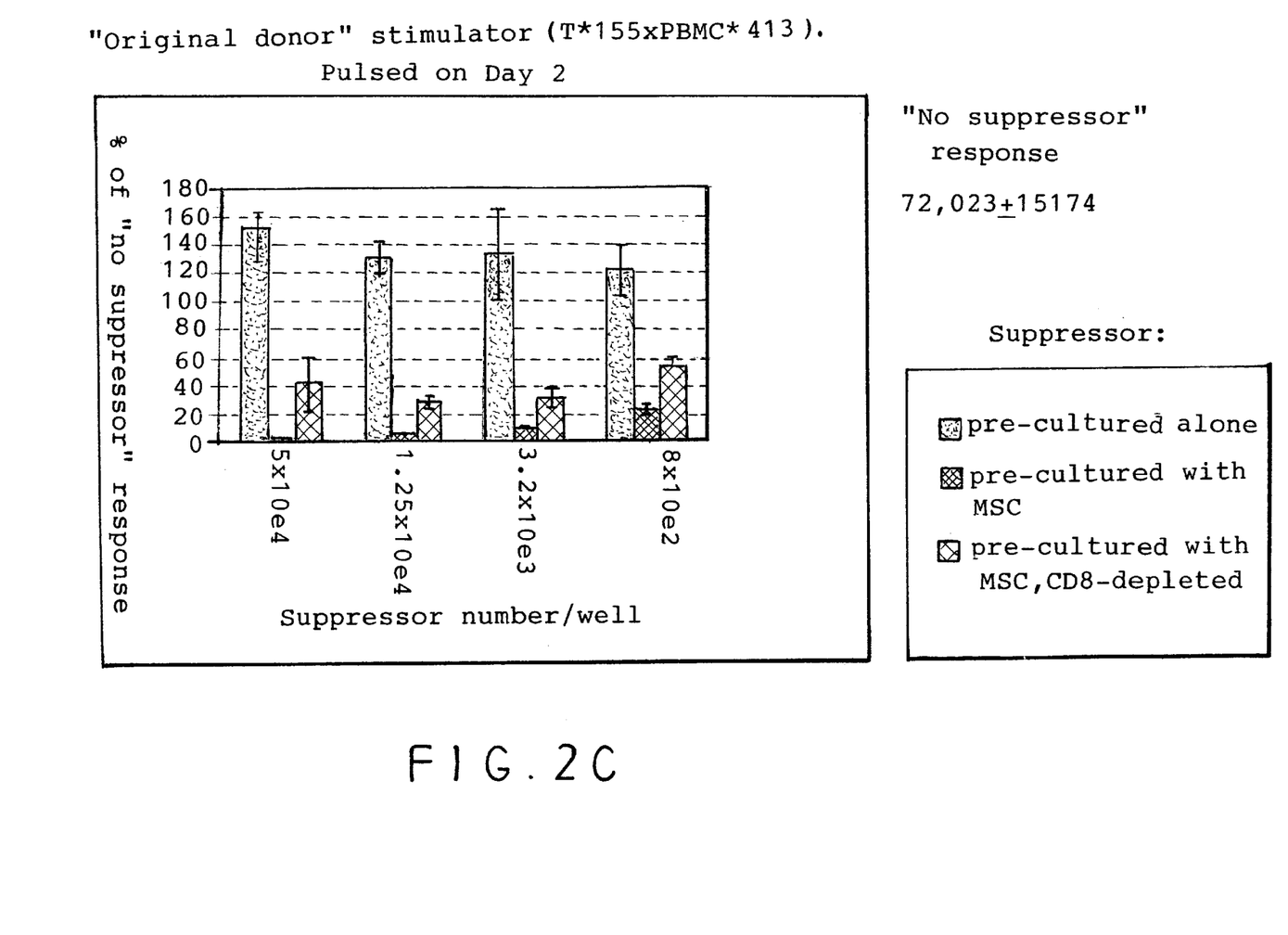
Figure 3A:
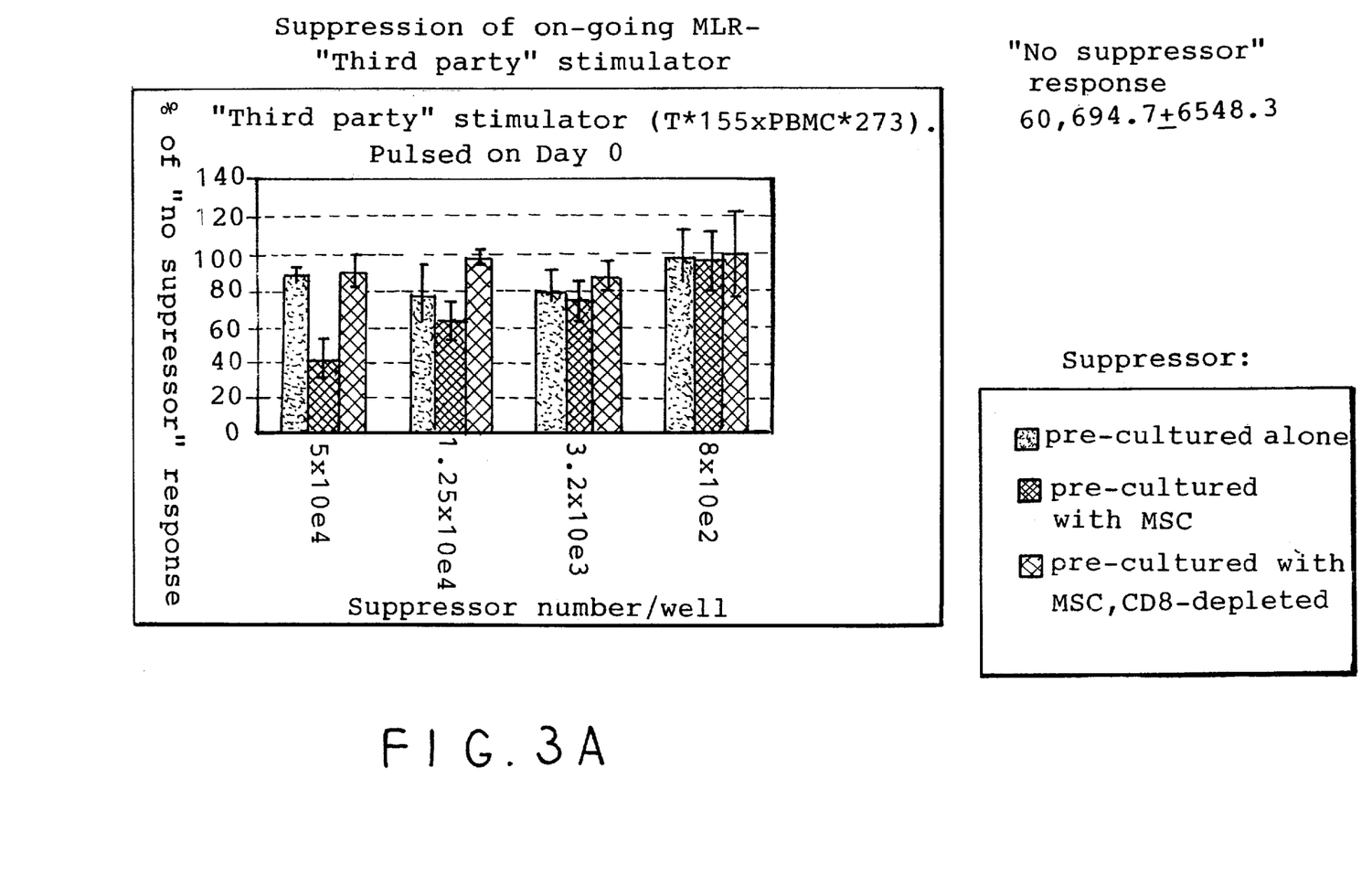
Figure 3B:
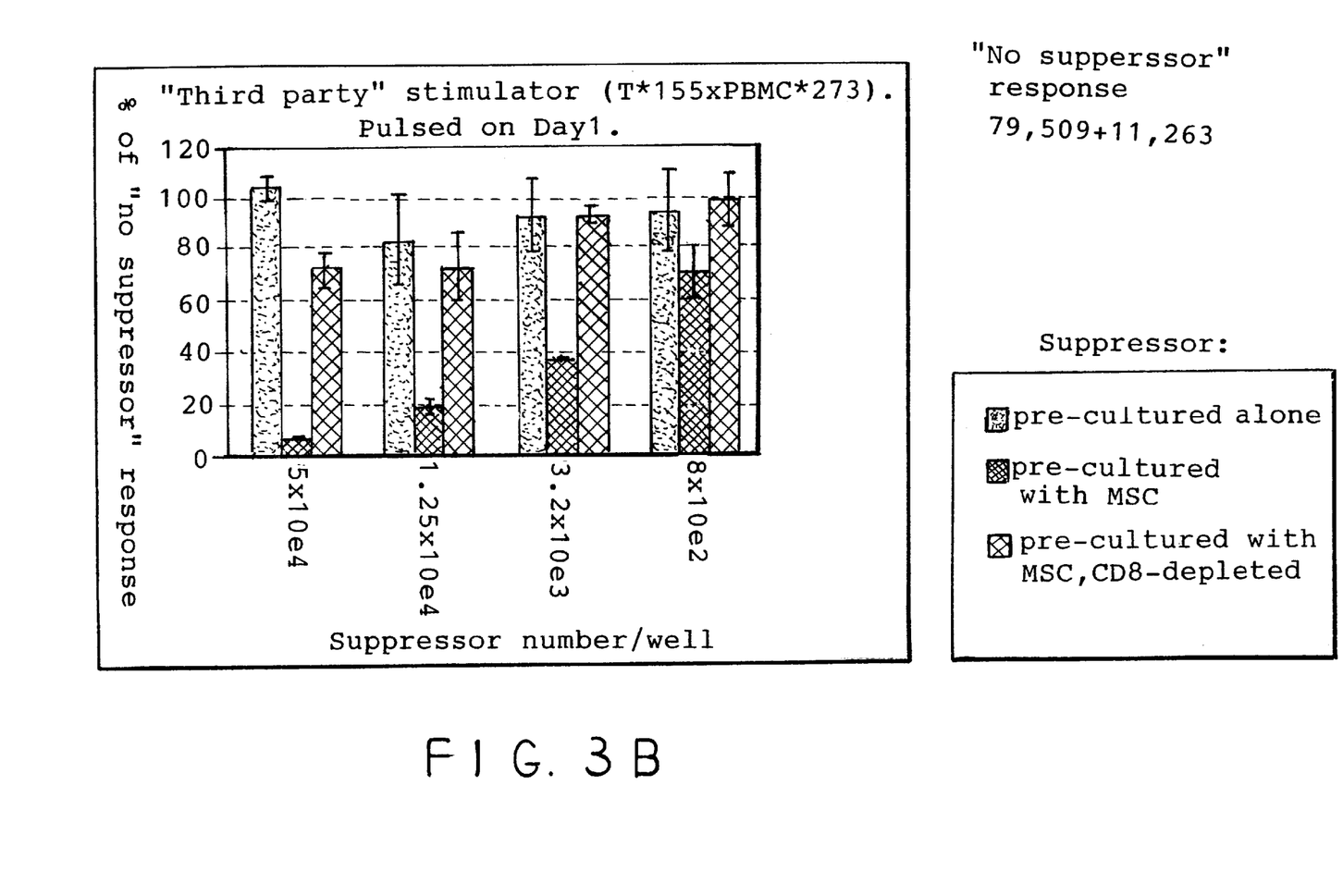
Figure 3C:
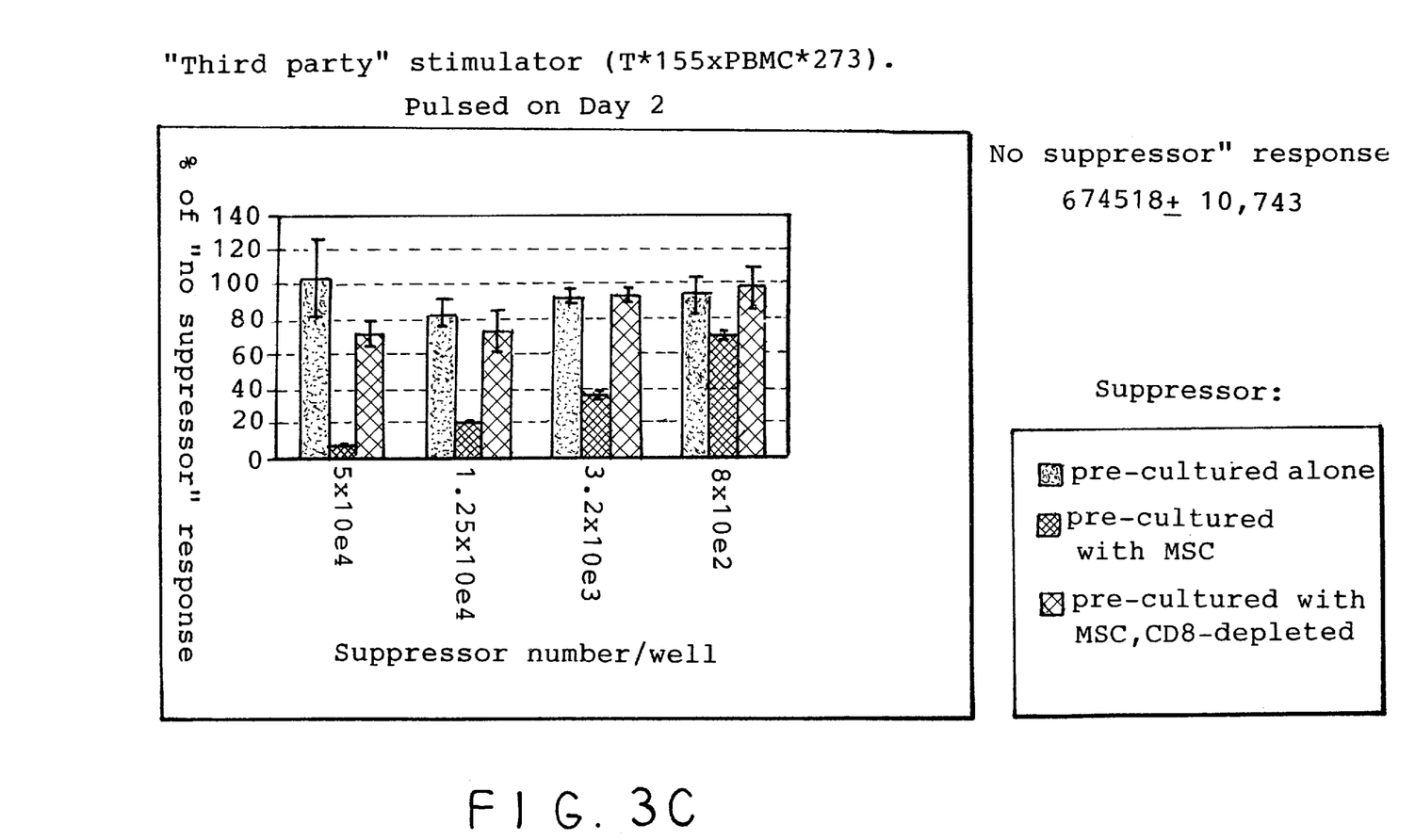

The results are shown in FIGS. 2 and 3. Suppressor T cells ("precultured with MSC") suppressed an on-going mixed lymphocyte reaction early and at a very low cell number per well. Depletion of CD8+ cells resulted in delayed and only partial suppression, thereby suggesting that suppressor cells were CD8+. T cells cultured without MSCs ("precultured alone") did not suppress and even enhanced the mixed lymphocyte reaction. The suppressive effect of the suppressor T cells was observed in a mixed lymphocyte reaction induced by the same stimulator cells (FIG. 2) as well as third party stimulators (FIG. 3).

Suppression of PHA-induced Proliferation by Pre-activated T Cells Cultured with MSCs:

PBMC from donor 155 (autologous to suppressor cells) at $5 \times 10^4$ cells/well were stimulated with PHA-M (5 µg/ml) in the presence or absence of suppressor T cells. T cells from donor 155 were pre-activated by irradiated PBMC from donor 413 for 7 days as described above. These cells were cultured alone or with MSCs from donor 273 for 3 days (non-fractionated or CD8 depleted). Suppressor T cells were added at different number/well (from $5 \times 10^4$ cells/well to $1.56 \times 10^3$ cells/well). Cultures were incubated for 1, 2 or 3 days, then pulsed with [$H^3$]TdR (5 Ci/mmol, 1 µCi/well) for an additional 18 hours.

Figure 4A:
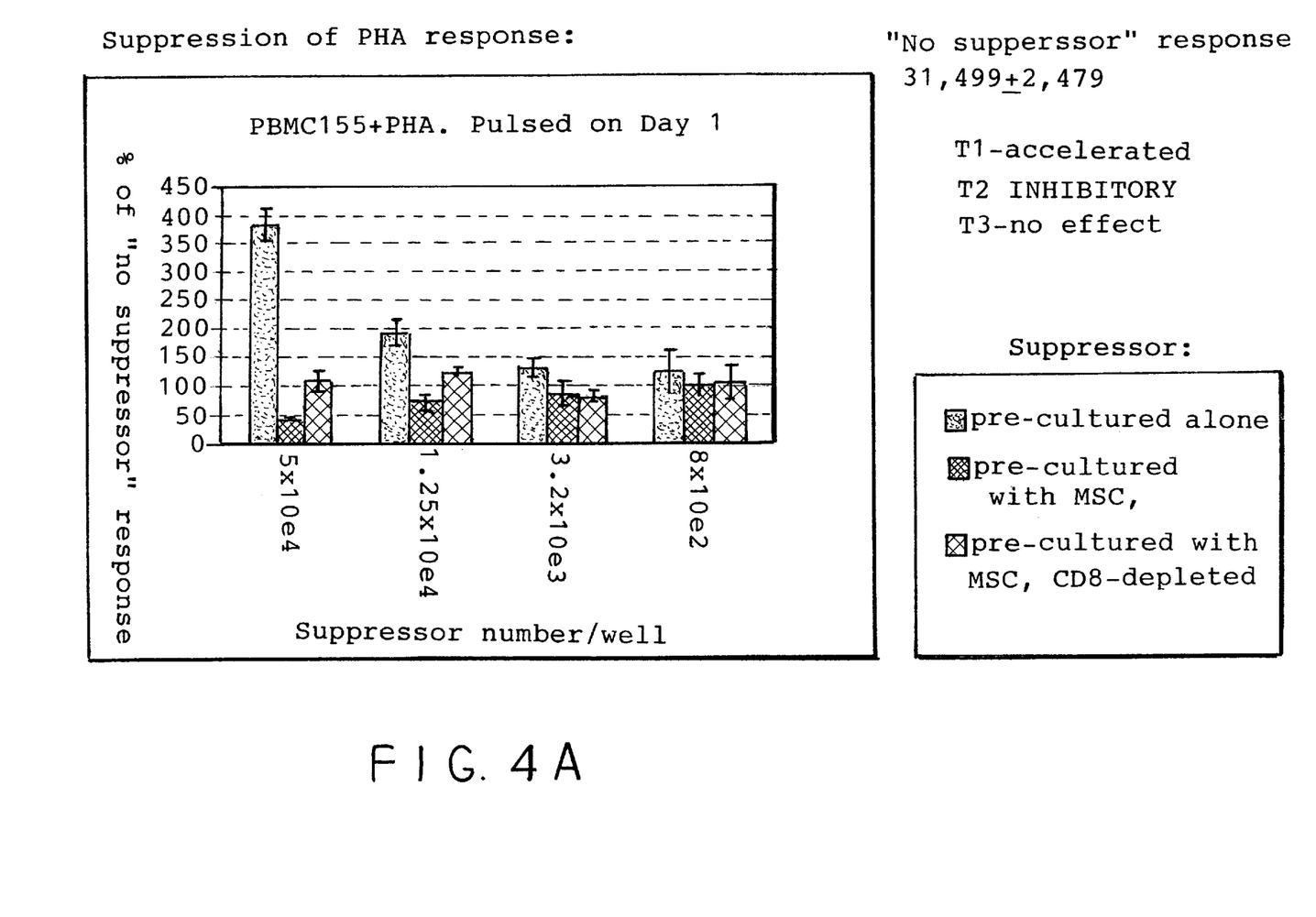
Figure 4B:
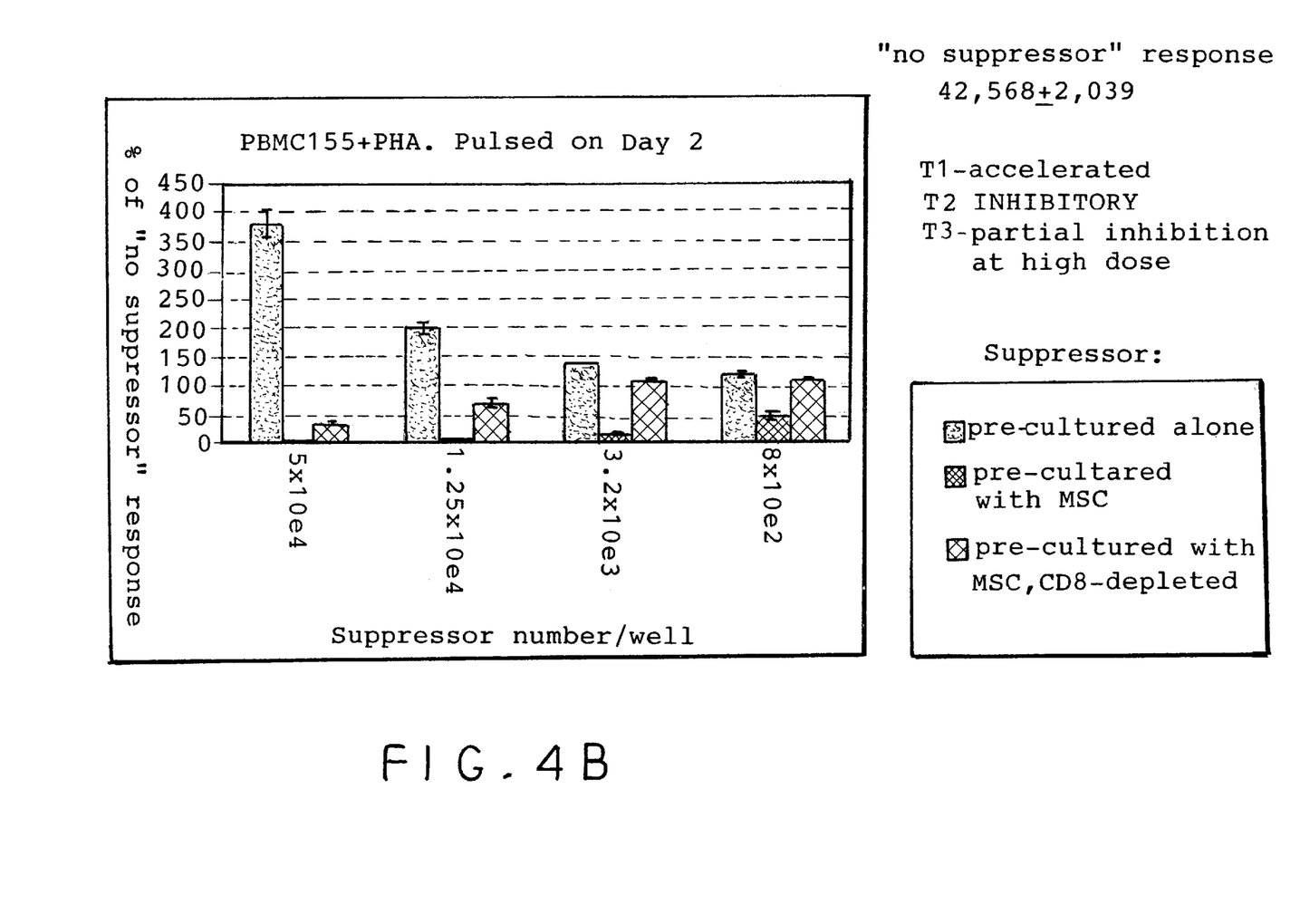
Figure 4C:
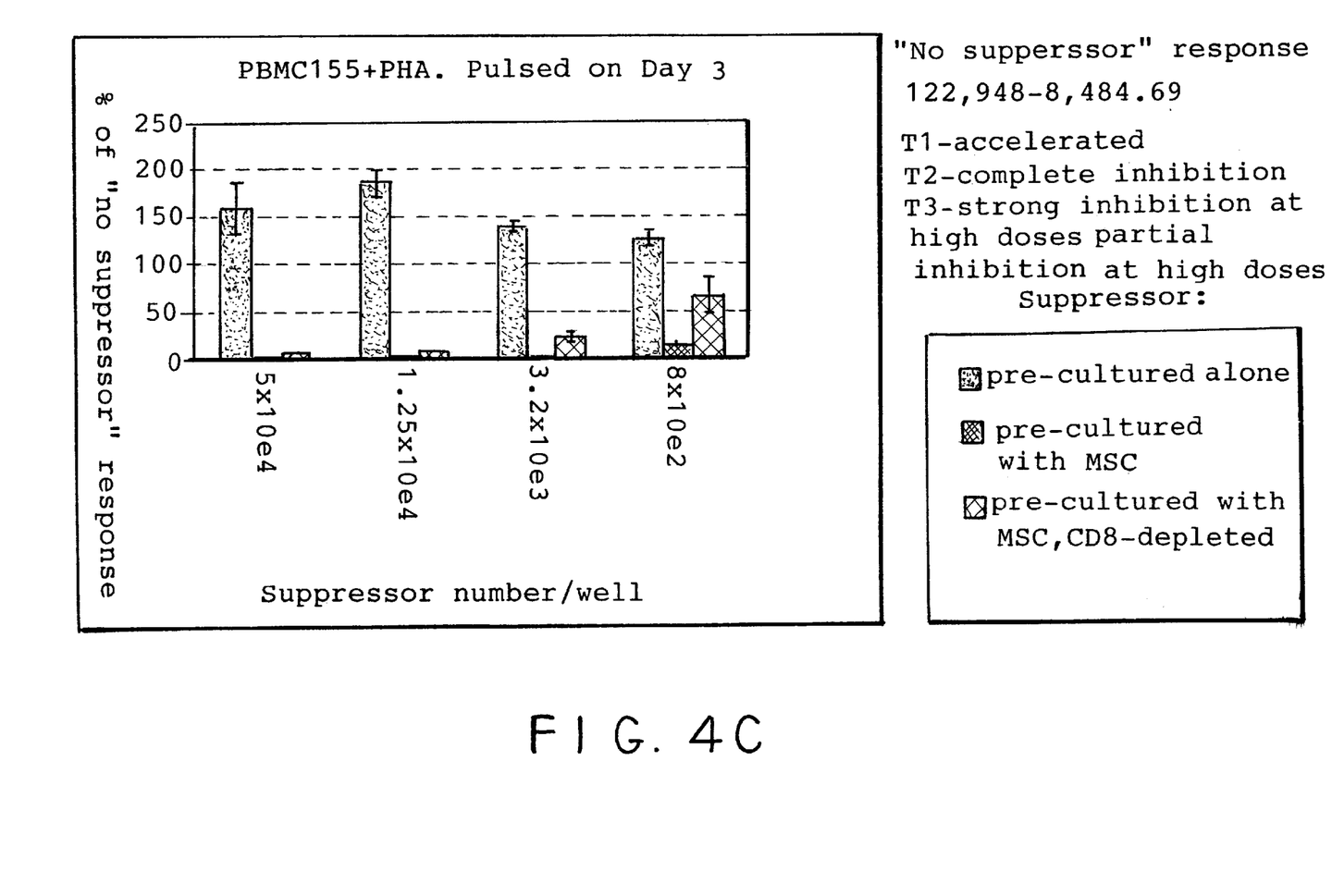

The results are shown in FIG. 4. Suppressor T cells suppressed PHA-induced proliferation of autologous PBMCs whereas T cells cultured alone accelerated the PHA response. Depletion of CD8 cells resulted in delayed and only partial suppression.

What is claimed is:

1. A method of reducing an immune response against an alloantigen, comprising:
   (a) culturing activated human T-cells with human mesenchymal stem cells in vitro, whereby said human mesenchymal stem cells induce said activated human T-cells to become human suppressor T-cells; and
   (b) contacting immune effector cells with said human suppressor T-cells in an amount effective to reduce the immune response.

2. The method of claim 1 wherein the effector cells are T-cells.

3. A method of treating a transplant recipient for graft versus host disease, comprising:
   (a) culturing activated human T-cells with human mesenchymal stem cells in vitro, whereby said human mesenchymal stem cells induce said activated human T-cells to become human suppressor T-cells; and
   (b) treating the recipient of a donor transplant with said human suppressor T-cells in an amount effective to reduce an immune response against the recipient by the transplant.

4. The method of claim 3, wherein the human suppressor T-cells are allogeneic to the human mesenchymal stem cells.

5. A method of reducing an immune response to a donor transplant, comprising:

(a) culturing activated human T-cells with human mesenchymal stem cells in vitro to produce human suppressor T-cells; and (b) administering to the recipient of the donor transplant said human suppressor T-cells in an amount effective to reduce an immune response in the recipient to the transplant.

6. The method of claim 5 wherein the human mesenchymal stem cells are allogeneic to the activated human T-cells.

7. The method of claim 5 wherein the transplant is a skin transplant.

8. The method of claim 5 wherein the human suppressor T-cells are administered to the recipient prior to administration of the transplant.

9. The method of claim 5 wherein the human suppressor T-cells are administered concurrently with administration of the transplant.

10. The method of claim 5 wherein the human suppressor T-cells are administered as part of the transplant.

11. The method of claim 5 wherein the human suppressor T-cells are administered after the transplant.

12. The method of claim 5 wherein the human suppressor T-cells are administered to the transplant recipient to treat rejection of the transplant by the recipient.

13. The method of claim 5 wherein the transplant is a solid organ.

14. The method of claim 5 wherein said solid organ is selected from the group consisting of heart, pancreas, kidney, lung and liver.

* * * * *